United States Patent [19]

Vacca et al.

[11] Patent Number: 5,559,239

[45] Date of Patent: Sep. 24, 1996

[54] PROCESS FOR PREPARING CARBAMOYL PYRIDINIUM COMPOUNDS

[75] Inventors: Paolo Vacca, Vado Ligure; Marco Frezzati, Savona, both of Italy

[73] Assignee: Minnesota Mining and Manufacturing Company, St. Paul, Minn.

[21] Appl. No.: 459,782

[22] Filed: Jun. 2, 1995

[30] Foreign Application Priority Data

Jul. 12, 1994 [EP] European Pat. Off. ............ 94110803

[51] Int. Cl.$^6$ ................................................ C07D 213/81
[52] U.S. Cl. ............................................ 546/323; 546/314
[58] Field of Search ................................ 546/314, 323

[56] References Cited

U.S. PATENT DOCUMENTS 4,063,952 12/1977 Himmelmann et al. .
4,414,309 11/1983 Langen et al. ............................ 430/551

FOREIGN PATENT DOCUMENTS 290879 6/1991 Germany .
290879A5 6/1991 Germany .

OTHER PUBLICATIONS

Abstract of Japanese Patent JP 1066162 published Mar. 13, 1989.

*Primary Examiner*—Melvyn I. Marquis
*Assistant Examiner*—D. Aylward
*Attorney, Agent, or Firm*—Gary L. Griswold; Walter N. Kirn; Mark A. Litman

[57] ABSTRACT

A process for synthesizing carbamoyl pyridinium compounds is described, in which the pyridine ring carries a sulfoalkyl group. The process comprises reacting a pyridine sulfonic acid with a carbamoyl chloride in the presence of a tert.-amine compound in a ketone solvent. The reactants are highly soluble in the ketone solvent, while, on the contrary, the carbamoyl pyridinium compounds and the tert.-ammonium halides formed by the reaction are not soluble in the ketone solvent and can be recovered from the reaction mixture. In a subsequent washing step with a selective solvent, for example in methanol in which carbamoyl pyridinium compounds are not soluble but tert.-ammonium halides are highly soluble, substantially pure carbamoyl pyridinium compounds can be obtained in high yields.

12 Claims, No Drawings

PROCESS FOR PREPARING CARBAMOYL PYRIDINIUM COMPOUNDS

FIELD OF THE INVENTION

The present invention relates to a process for preparing carbamoyl pyridinium compounds and, more particularly, sulfo-substituted carbamoyl pyridinium compounds.

BACKGROUND OF THE INVENTION

Photographic light-sensitive materials make use of proteins and, in particular, gelatin as binders. For example, gelatin is used as the main component of silver halide emulsion layers, protective layers, filter layers, intermediate layers, antihalation layers, backing layers and subbing layers of photographic light-sensitive materials.

It is known that the mechanical properties of gelatin containing layers of photographic materials can be improved by addition of a hardening agent. In fact, the photographic materials are usually stored at elevated temperatures and humidity conditions or treated with various aqueous solutions having different pH's and temperatures, and gelatin layers which have not been treated with a hardening agent have poor water resistance, heat resistance and abrasion resistance.

Many compounds are known to be effective for increasing mechanical resistance of a gelatin layer by hardening. They include, for example metal salts such as chromium, aluminium and zirconium salts; aldehydes such as formaldehyde and glutaraldehyde; halogenocarboxylaldehydes such as mucochloric acid; aziridine compounds such as those described in U.S. Pat. No. 3,017,280; epoxy compounds such as those described in U.S. Pat. No. 3,091,537; halogenotriazine compounds such as hydroxydichlorotriazine and aminodichlorotriazine; compounds having vinylsulfonyl groups such as methylene-bis-vinylsulfone, divinylsulfone and methylenebis-vinylsulfonamide.

A group of hardening agents for photographic gelatin-containing layers which is particularly interesting has been disclosed in U.S. Pat. No. 4,063,952. These hardening agents are carbamoyl pyridinium compounds in which the pyridine ring carries a sulfo or sulfoalkyl group. These compounds have high water solubility, a fast hardening action for gelatin and low occurrence of post-hardening (post-hardening is a change in the degree of hardening caused by slow continued hardening of the gelatin). They belong to the group of "quick-acting" hardeners with which the light-sensitive photographic materials can be hardened to an optimum degree within a very short time.

U.S. Pat. No. 4,063,952 describes a method of preparation of said carbamoyl pyridinium compounds in which the pyridine ring carries a sulfo or sulfoalkyl group. According to that method, the alkali metal salt of a pyridine carrying a sulfo or a sulfoalkyl group is reacted with a carbamoyl halide in the presence of a mixture of dimethylformamide and methanol as solvents, and the reaction product (which may partly precipitate) is actively precipitated by addition of ethyl ether. Alkali metal halide, which is a by-product of this reaction, precipitates together with the carbamoyl pyridinium compound. Accordingly, U.S. Pat. No. 4,063,952 describes the hardening agent by the formula:

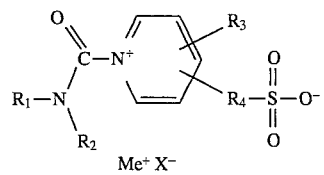

in which $R_1$ and $R_2$ each represents an alkyl group, an aryl group, or an aralkyl group, or $R_1$ and $R_2$ together represent the groups required to complete a piperidine or a morpholine ring, $R_3$ represents hydrogen, methyl or ethyl, $R_4$ represents methylene, ethylene, propylene or a single chemical bond, $Me^+$ represents an alkali metal cation such as $Li^+$, $Na^+$ or $K^+$ and $X^-$ represents an anion such as $Cl^-$ or $Br^-$.

The presence of an alkali metal halide in the hardening agent may cause problems in the photographic material using said hardening agent. In fact, the saline content in the photographic material is increased, thus increasing a tendency of the photographic material to stick when stored in rolls or sheets. Additionally, it is well known that halide ions, such as chloride, bromide or iodide ions may change the photographic characteristics of the silver halide emulsions.

J01-066,162 describes a synthesis of carbamoyl pyridinium compounds, in which the pyridine ring carries a sulfo or sulfoalkyl group. The process comprises forming the inner salt of a pyridine sulfonic acid in the presence of a tert.-amine compound and reacting the inner salt with a carbamoyl chloride. By this synthesis, hardening agents free of inorganic salts, e.g., NaCl and KCl, are obtained.

DD 290,879 describes a synthesis of carbamoyl pyridinium compounds in which the pyridine ring carries a sulfoalkyl group which comprises reacting a pyridine sulfonic acid with a carbamoyl chloride in a nitrile solvent in the presence of a tert.-amine compound. As nitrile solvents, acetonitrile, propionitrile, butyronitrile and benzonitrile are mentioned. The purpose of DD 290,879 is to provide a solvent in which the reactants and the tert.-ammonium halides obtained as by-products of the reaction are soluble, and the carbamoyl pyridinium compounds are insoluble. It has been found, however, that the carbamoyl piridinium compounds still contain, after the reaction, significant amounts of tert.-ammonium halides, which can be eliminated by subsequent washing steps with the nitrile solvent. The yield of pure carbamoyl pyridinium compound is consequently lowered.

SUMMARY OF THE INVENTION

A process has been found for preparing carbamoyl pyridinium compounds, in which the pyridine ring carries a sulfoalkyl group, which process comprises reacting a pyridine sulfonic acid with a carbamoyl chloride in the presence of a tert.-amine compound in a ketone solvent. The reactants are highly soluble in the ketone solvent, while the carbamoyl pyridinium compounds and the tert.-ammonium halides formed by the reaction are not soluble in the ketone solvent and can be recovered from the reaction mixture. In a subsequent washing step in a selective solvent, for example in methanol in which carbamoyl pyridinium compounds are not soluble but tert.-ammonium halides are highly soluble,

3 pure carbamoyl pyridinium compounds can be obtained in high yields.

DETAILED DESCRIPTION OF THE INVENTION

The process for preparing a carbamoyl pyridinium compound of the present invention comprises the steps of:

a) reacting a pyridine sulfonic acid compound with a carbamoyl halide in the presence of a tert.-amine compound in a ketone solvent to form a carbamoyl pyridinium compound, b) recovering from the reaction mass a mixture of the carbamoyl pyridinium compound and tert.-ammonium halide, and c) separating the carbamoyl pyridinium compound from the tert.-ammonium halide by washing the mixture with a selective solvent for the tert.-ammonium halide.

By selective solvent is meant a solvent which has a much higher solvating activity towards the tert.-ammonium halide than for the carbamoyl pyridinium compound. It is preferred that the selective solvent (in terms of grams compound/ml of solvent) provides a ratio of the solubility for the halide to the ratio of the solubility for the carbamoyl pyridinium of at least 5/1, more preferably at least 10/1, and most preferably at least 20/1 or even at least 50/1.

Carbamoyl halides useful in this invention correspond to the following formula:

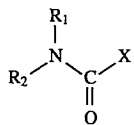

in which $R_1$ and $R_2$ (which may be the same or different) each represents an alkyl group having: from 1 to 10 carbon atoms (e.g., methyl, ethyl, 2-ethylhexyl), an aryl group having from 6 to 15 carbon atoms (e.g., phenyl, naphthyl), an aralkyl group having from 7 to 15 carbon atoms (e.g., benzyl, phenethyl), or R1 and R2 together form the atoms required to complete a heterocyclic ring (e.g., pyrrolidine, morpholine, piperidine, piperazine, 1,2,3,4-tetrahydroquinoline ring, etc.). X represents an halogen atom (e.g., Cl, Br).

When the term "group" or "ring" is used in the present invention, the described chemical material includes the basic group or ring and that group or ring with conventional substituents. Where the term "moiety" is used to describe a chemical compound or substituent, only an unsubstituted chemical material is intended to be included. For example, "alkyl group" includes not only such alkyl moieties as methyl, ethyl, octyl, stearyl, etc. but also such moieties bearing substituents groups such as halogen, cyano, hydroxyl, nitro, amine, carboxylate, etc. On the other hand, "alkyl moiety" includes only methyl, ethyl, octyl, stearyl, cyclohexyl, etc.

Pyridine sulfonic acid compounds useful in this invention correspond to the following general formula:

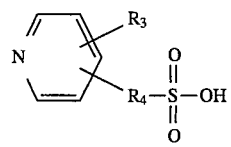

in which $R_3$ represents a substituents such as a hydrogen atom, a halogen atom, an alkyl group having from 1 to 10 carbon atoms (e.g., methyl, ethyl), an alkoxy group having from 1 to 10 carbon atoms, a carbamoyl group, a ureido group. R4 represents an alkylene group having from 1 to 4 carbon atoms (e.g., methylene, ethylene, propylene) or a single chemical bond.

Tert.-amine compounds useful in the process of present invention correspond to the following general formula:

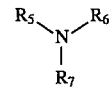

in which $R_5$, $R_6$ and $R_7$ (which may be the same or different) each represents an alkyl group having from 1 to 10 carbon atoms .(e.g., methyl, ethyl, 2-ethylhexyl), an aryl group having from 6 to 15 carbon atoms (e.g., phenyl, naphthyl), or a cycloalkyl group having from 5 to 8 ring carbon atoms (e.g., cyclohexyl).

The solvents useful in the process of the present invention are those organic liquids in which the reactants (i.e., the carbamoyl halides, the pyridine sulfonic acids and the tert.-amine compounds) are highly soluble over a wide range of temperatures, and in which, on the contrary, the carbamoyl pyridinium compounds and the tert.-ammonium halides are not soluble. Representative solvents which are useful in this invention include ketone compounds such as acetone, diethyl ketone, methyl ethyl ketone, methyl iso-propyl ketone, cyclopentanone, methyl iso-butyl ketone and mixtures thereof. For reasons of economy and availability, acetone is particularly useful as solvent. The reaction is completed in few hours (1 to 3) at low reaction temperatures (e.g., at the boiling point of the solvent). At the end of the reaction, the reaction mixture is cooled at room temperature (i.e., 25° C.) and the carbamoyl pyridinium compound and the tert.-ammonium halide are recovered from the remaining reaction mixture by filtration or centrifugation. As a subsequent step in the process of the present invention, the mixture of carbamoyl ammonium compound and tert.-ammonium halide is subjected to washing with a selective solvent for the tert.-ammonium halide. Representative selective solvents for the tert.-ammonium halide include aliphatic alcohols, such as methanol, ethanol and mixtures thereof. For reasons of economy, methanol is particularly useful as a selective solvent for the tert.-ammonium halides. Washing is performed by stirring the mixture of carbamoyl pyridinium compound and tert.-ammonium halide in the selective solvent (alone or in mixture with the ketone solvent) and recovering the relatively insoluble carbamoyl pyridinium compound by filtration or centrifugation. These purification steps may be performed one or more times, as necessary. Usually, however, one single purification step permits separation of carbamoyl pyridinium compound which contains less than 1% by weight of tert.-ammonium halide.

The process of the present invention may be effected in a batch or a continuous type operation. For example, when a batch type operation is used, the pyridine sulfonic acid compound and the tert.-amine compound and a quantity of the ketone solvent are placed in an appropriate apparatus such as a jacketed reaction kettle equipped with a stirring mechanism and agitated. The carbamoyl halide is added to the reaction mixture, and the mixture is heated to the desired reaction temperature and maintained thereat for the duration of the reaction. At the end of the reaction, the carbamoyl pyridinium compound is recovered and subjected to washing as described.

It is contemplated within the scope of the present invention that the preparation of carbamoyl pyridinium compounds by the reaction of pyridine sulfonic acid compounds and carbamoyl halides may also be effected in a continuous manner, although not necessarily with equivalent results. For example, when a continuous type operation is used, the starting materials dissolved in the ketone solvent are fed continuously to a reaction zone which is maintained at proper operating conditions of temperature and stirring. After a desired residence time, the reaction mixture is continuously discharged to isolate the desired carbamoyl pyridinium compound.

The carbamoyl pyridinium compounds of the process of the present invention correspond to the general formula:

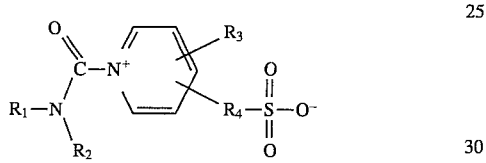

in which $R_1$, $R_2$, $R_3$ and $R_4$ represent substituents as defined for formulas above.

Practical examples of carbamoyl pyridinium compounds which can be prepared using the process of this invention are illustrated below, but the invention is not limited to these compounds.

H-1
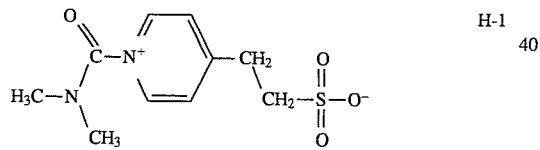

H-2
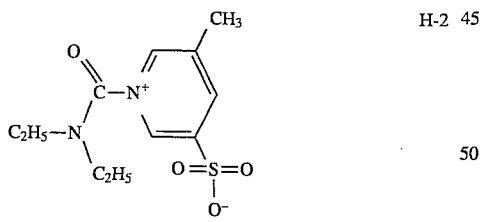

H-3
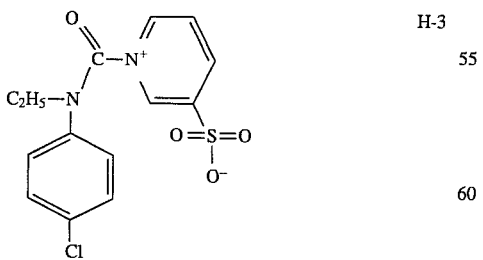

H-4
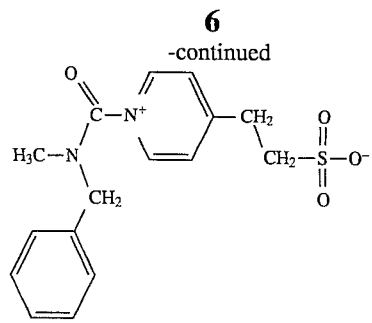

H-5
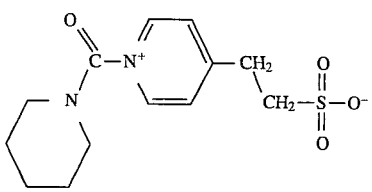

H-6
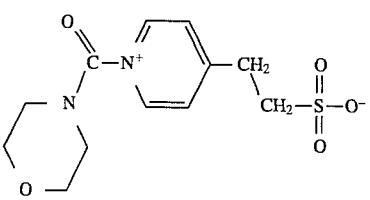

H-7
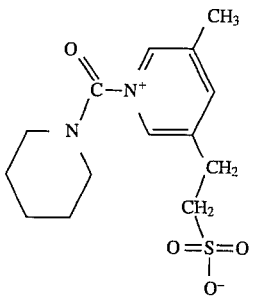

H-8
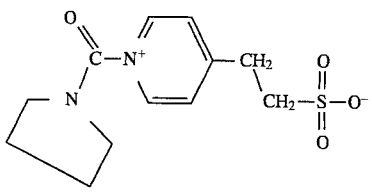

H-9
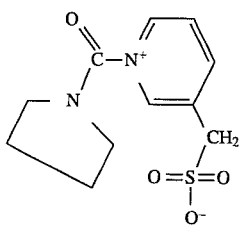

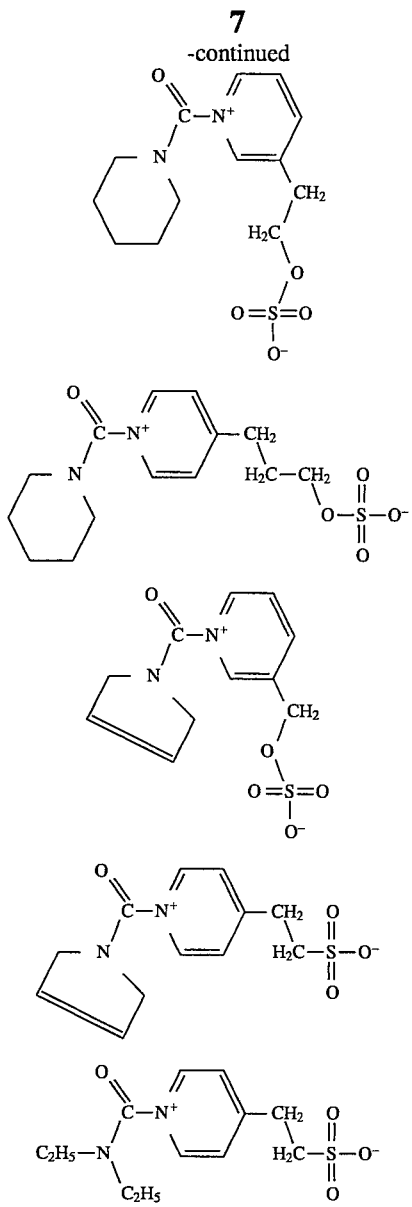

The following examples are given to illustrate the process of the present invention, but are not intended to limit the scope of the present invention in any manner whatsoever.

EXAMPLE 1 (COMPARISON)

9.35 g (0.05 mol) of pyridine-4-ethanesulfonic acid and 5.06 g (0.05 mol) of triethylamine were dissolved in 50 ml of acetonitrile and heated to reflux. 5.35 g (0.05 mol) of N,N-dimethylcarbamoyl chloride were added dropwise. The mixture was heated at reflux for I hour, then suction filtered. The precipitate was washed three times with 60 ml of acetonitrile at reflux, suction filtered and dried. The yield was 5 g (38.8%) of a mixture of the hardening agent corresponding to formula HI and 28.8% mol of triethylammonium chloride.

EXAMPLE 2 (COMPARISON)

18.7 g (0.1 mol) of pyridine-4-ethanesulfonic acid and 10.12 g (0.1 mol) of triethylamine were dissolved in 100 ml of dimethylformamide and heated to 85° C. Then, 10.7 g (0.1 mol) of N,N-dimethylcarbamoyl chloride were added and the mixture was stirred at 85° C. for 2 hours. The precipitate was suction filtered, washed with dimethylformamide, suction filtered and dried. The yield was 7.5 g (29%) of a mixture of the hardening agent corresponding; to formula HI and 20.3% mol of pyridine-4-ethanesulfonic acid.

EXAMPLE 3 (INVENTION)

46.85 g (0.25 mol) of pyridine-4-ethanesulfonic acid and 25.3 g (0.25 mol) of triethylamine were dissolved in 350 ml of acetone and heated to reflux. Then, 26.9 g (0.25 mol) of N,N-dimethylcarbamoyl chloride were added and the mixture was stirred at reflux for I hour. The precipitate was suction filtered, washed with a mixture of 125 ml of acetone and 125 ml of methanol at reflux, suction filtered and dried. The yield was 46.5 g (72% ) of the hardening agent corresponding to formula HI containing less than 1% mol of triethylammonium chloride.

EXAMPLE 4 (INVENTION)

18.7 g (0.1 mol) of pyridine-4-ethanesulfonic acid and 10.12 g (0.1 mol) of triethylamine were dissolved in 350 ml of acetone and heated to reflux. Then, 13.6 g (0.1 mol) of N,N-diethylcarbamoyl chloride were added and the mixture was stirred at reflux for I hour. The precipitate was suction filtered, washed with a mixture of 50 ml of acetone and 50 ml of methanol at reflux, suction filtered and dried. The yield was 18.0 g (62%) of the hardening agent corresponding to formula HI4 containing less than 1% mol of triethylammonium chloride.

We claim:

1. Process for synthesizing a carbamoyl pyridinium compound comprising the steps of:

a) reacting a pyridine sulfonic acid compound with a carbamoyl halide in the presence of a tert.-amine compound in a ketone solvent to form a mixture comprising carbamoyl pyridinium compound and a tert.-ammonium halide, b) recovering from the reaction mass a mixture of the carbamoyl pyridinium compound and the tert.-ammonium halide, and c) separating the carbamoyl pyridinium compound from the tert.-ammonium halide by washing the mixture with a selective solvent for the tert.-ammonium halide.

2. Process according to claim 1, wherein the ketone solvent is acetone.

3. Process according to claim 1, wherein the selective solvent is methanol.

4. Process according to claim 1, wherein the carbamoyl halide corresponds to the formula:

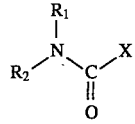

wherein $R_1$ and $R_2$ (which may be the same or different) each represents an alkyl group having from 1 to 10 carbon atoms, an aryl group having from 6 to 15 carbon atoms, an aralkyl group having from 7 to 15 carbon atoms, or R1 and R2 together form the atoms required to complete a heterocyclic ring, and X represents an halogen atom.

5. Process according to claim 1, wherein the pyridine sulfonic acid compound corresponds to the formula:

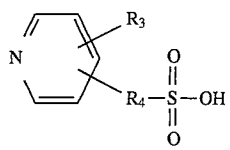

wherein:

$R_3$ represents a hydrogen atom, a halogen atom, an alkyl group having from 1 to 10 carbon atoms, an alkoxy group having from 1 to 10 carbon atoms, a carbamoyl group, or a ureido group, and $R_4$ represents an alkylene group having from 1 to 4 carbon atoms or a single chemical bond between a pyridinium ring and a sulfonic acid moiety.

6. Process according to claim 1, wherein the tert.-amine compound corresponds to the formula:

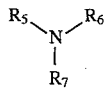

wherein:

$R_5$, $R_6$ and $R_7$ (which may be the same or different) each represents an alkyl group having from 1 to 10 carbon atoms, an aryl group having frown 6 to 15 carbon atoms, or a cycloalkyl group having from 5 to 8 carbon atoms.

7. Process according to claim 1, for preparing a carbamoyl pyridinium compound corresponding to the formula:

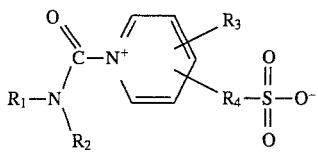

wherein $R_1$ and $R_2$ (which may be the same or different) each represents an alkyl group having from 1 to 10 carbon atoms, an aryl group having from 6 to 15 carbon atoms, an aralkyl group having from 7 to 15 carbon atoms, or $R_1$ and $R_2$ together form the atoms required to complete a heterocyclic ring, $R_3$ represents a hydrogen atom, a halogen atom, an alkyl group having from 1 to 10 carbon atoms, an alkoxy group having from 1 to 10 carbon atoms, a carbamoyl group, or a ureido group, and $R_4$ represents an alkylene group having from 1 to 4 carbon atoms or a single chemical bond between a pyridinium ring and a sulfonic acid moiety.

8. The process of claim 3 wherein the ketone solvent is acetone.

9. The process of claim 4 wherein the ketone solvent is acetone.

10. The process of claim 5 wherein the ketone solvent is acetone.

11. The process of claim 6 wherein the ketone solvent is acetone.

12. The process of claim 7 wherein the ketone solvent is acetone.

* * * * *